(12) United States Patent
Fischer et al.

(10) Patent No.: US 11,197,711 B2
(45) Date of Patent: Dec. 14, 2021

(54) TISSUE FUSION INSTRUMENT, IN PARTICULAR A TISSUE FUSION FORCEPS

(71) Applicant: ERBE ELEKTROMEDIZIN GMBH, Tuebingen (DE)

(72) Inventors: Klaus Fischer, Nagold (DE); Achim Brodbeck, Metzingen-Neuhaus (DE); Daniel Schaeller, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 195 days.

(21) Appl. No.: 16/379,485

(22) Filed: Apr. 9, 2019

(65) Prior Publication Data

US 2019/0298438 A1    Oct. 3, 2019

Related U.S. Application Data

(62) Division of application No. 13/552,769, filed on Jul. 19, 2012, now Pat. No. 10,820,938.

(30) Foreign Application Priority Data

Aug. 1, 2011    (EP) ...................................... 1176186

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/1412* (2013.01); *A61B 2018/1455* (2013.01)

(58) Field of Classification Search
CPC ............ A61B 18/1442; A61B 18/1445; A61B 2018/0063; A61B 2018/1412; A61B 2018/1455
See application file for complete search history.

(56) References Cited

U.S. PATENT DOCUMENTS

| | | | |
|---|---|---|---|
| 5,891,140 A | 4/1999 | Ginn et al. | |
| 6,679,882 B1 | 1/2004 | Kornerup | |
| 7,147,638 B2 | 12/2006 | Chapman et al. | |
| 2004/0236325 A1* | 11/2004 | Tetzlaff .............. | A61B 18/1445 606/51 |
| 2005/0010211 A1 | 1/2005 | Suzuki | |
| 2006/0259034 A1 | 11/2006 | Eder et al. | |
| 2006/0264922 A1 | 11/2006 | Sartor et al. | |
| 2007/0255279 A1 | 11/2007 | Buysse et al. | |
| 2007/0276363 A1 | 11/2007 | Patton et al. | |

(Continued)

FOREIGN PATENT DOCUMENTS

| | | |
|---|---|---|
| CN | 2721022 Y | 8/2004 |
| CN | 101999932 A | 4/2011 |
| EP | 1 348 391 A1 | 10/2003 |

*Primary Examiner* — Michael F Peffley
*Assistant Examiner* — Bo Ouyang
(74) *Attorney, Agent, or Firm* — Blank Rome LLP

(57) ABSTRACT

A tissue fusion instrument having electrodes that are only connected in a punctiform manner to their electrode carrier such that they are electrically conducting and thus, heat-conducting. As a result, heat transfer from the electrode to the respective electrode carrier is restricted. This, on one hand, benefits the desired surgical outcome and, on the other hand, prevents parasitic heating of the surgical instrument and concomitant damage to surrounding tissue.

15 Claims, 4 Drawing Sheets

(56) References Cited

U.S. PATENT DOCUMENTS

| | | |
|---|---|---|
| 2008/0140066 A1 | 6/2008 | Davison et al. |
| 2009/0112202 A1 | 4/2009 | Young |
| 2009/0182328 A1 | 7/2009 | D'Amelio et al. |
| 2009/0216229 A1* | 8/2009 | Chojin ............... A61B 18/1445 606/52 |
| 2009/0248007 A1 | 10/2009 | Falkenstein et al. |
| 2009/0299367 A1* | 12/2009 | Ginnebaugh ...... A61B 18/1445 606/51 |
| 2009/0318849 A1* | 12/2009 | Hobbs ............... A61M 25/0043 604/20 |
| 2010/0100122 A1 | 4/2010 | Hinton |
| 2010/0204698 A1 | 8/2010 | Chapman et al. |
| 2011/0028971 A1 | 2/2011 | Takashino et al. |

* cited by examiner

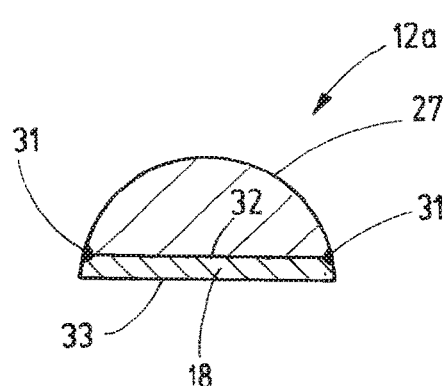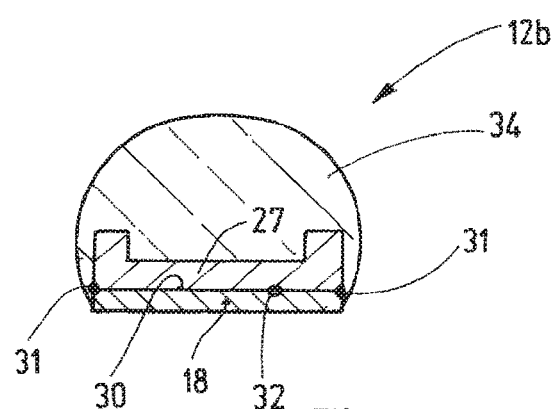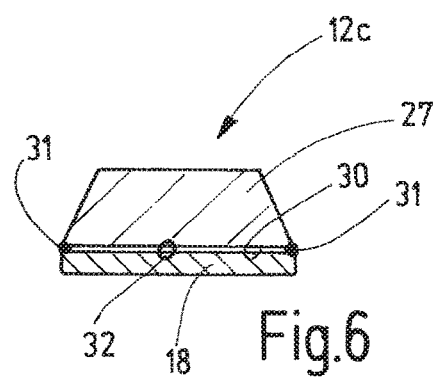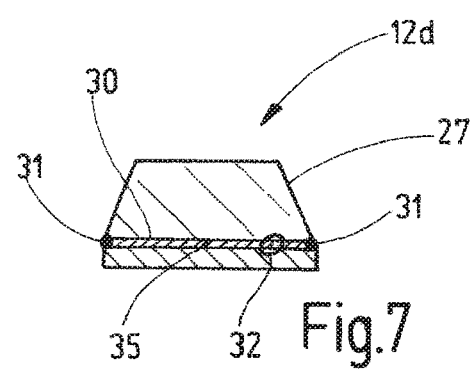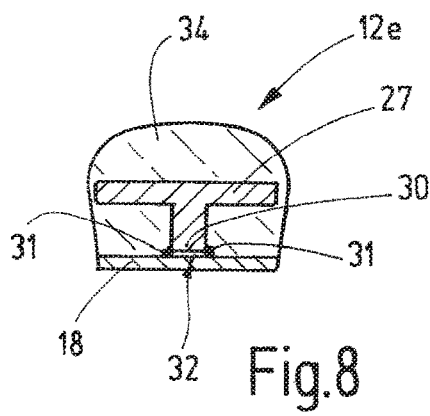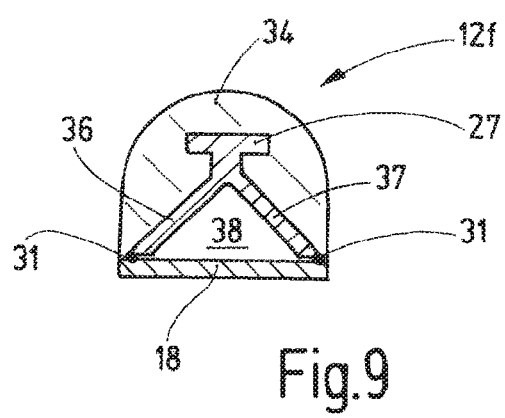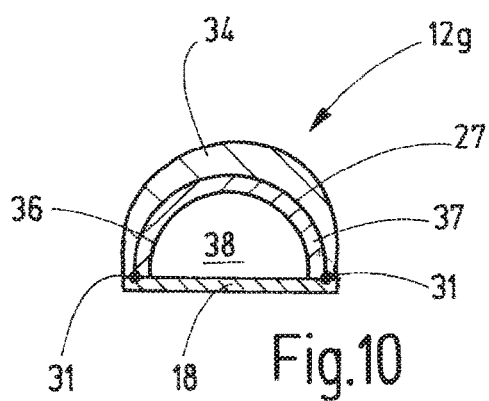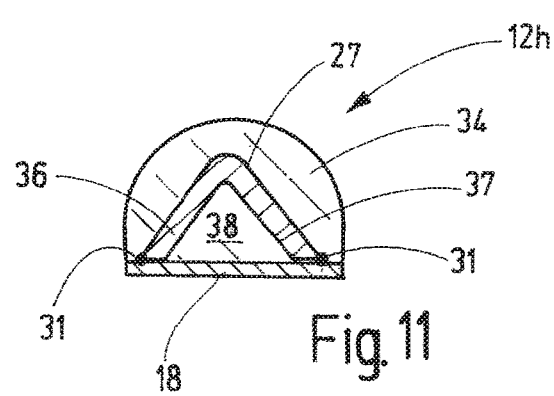

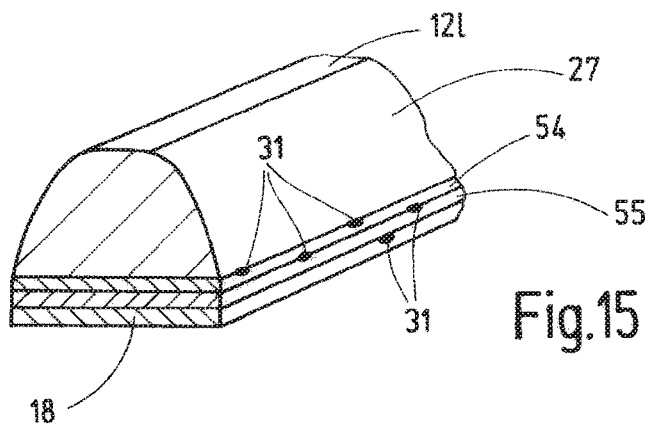
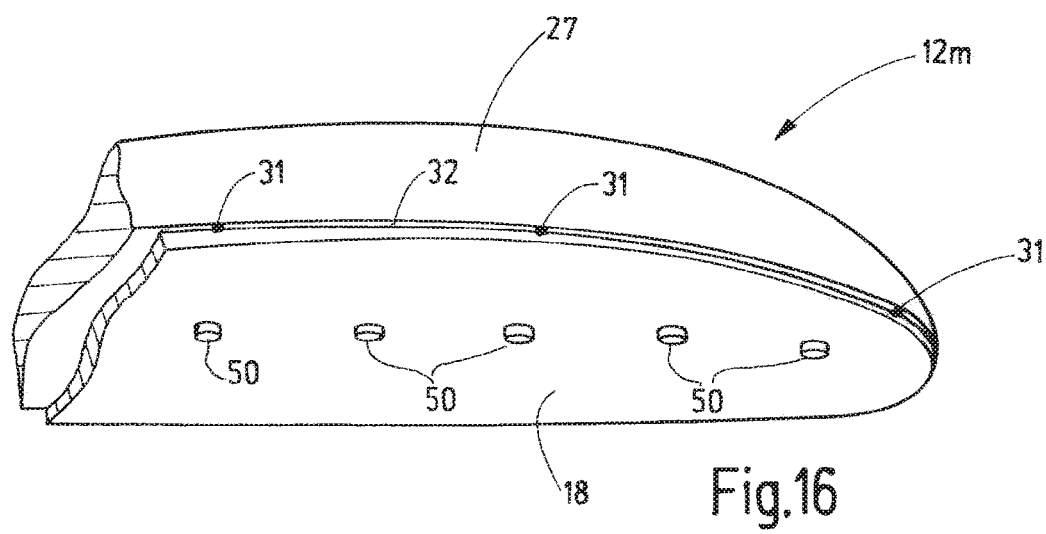
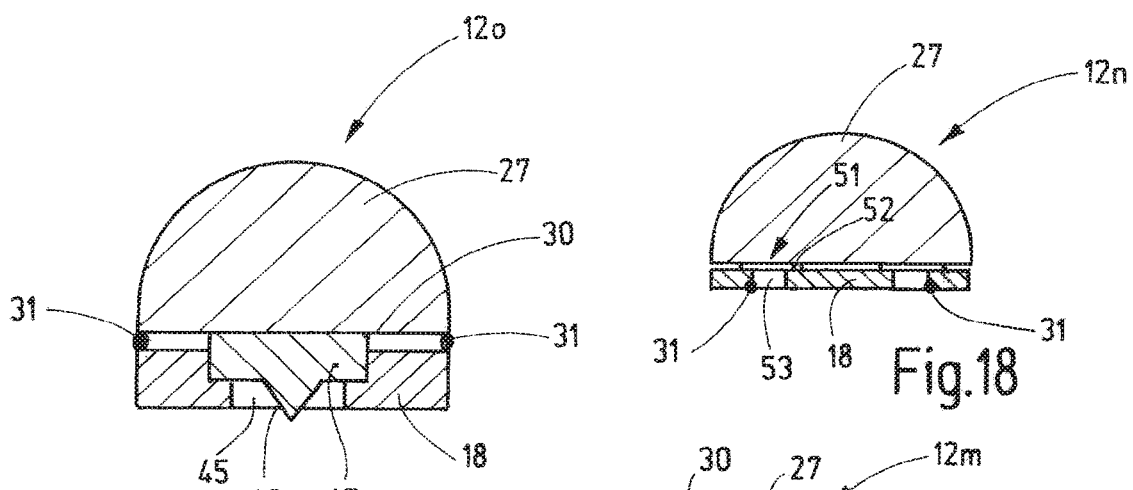
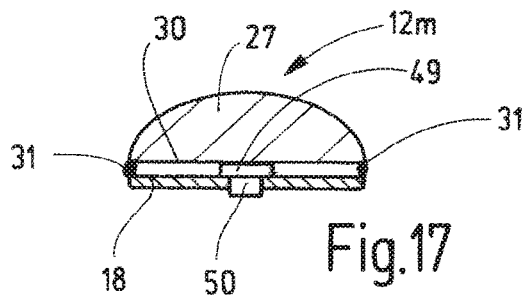

TISSUE FUSION INSTRUMENT, IN PARTICULAR A TISSUE FUSION FORCEPS

RELATED APPLICATION

This application is a divisional of U.S. patent application Ser. No. 13/552,769, filed on Jul. 19, 2012, which claims priority to European Patent Application No. 11176186.2 filed Aug. 1, 2011, the entirety of each of which are hereby incorporated by reference.

TECHNICAL FIELD

Embodiments disclosed herein relate to a tissue fusion instrument such as a tissue fusion forceps.

BACKGROUND

Tissue fusion instruments are used, for example, to clamp and seal blood vessels using current and the effects of heat. For example, vessel walls lying opposite one another are pressed against each other by two electrodes and heated by current flow such that they adhere to each other in the long term. Here, the effect of heat should be limited where possible to the tissue areas to be fused. The aim is to avoid adversely affecting or damaging surrounding tissue.

The basic design of a tissue fusion instrument is shown in US patent application publication 2006/0264922 A1, for example. The instrument is designed in the form of forceps with two arms electrically insulated from one another. A vessel can be gripped, clamped off and coagulated by the effect of the current between the two arms of the forceps.

To prevent the entry of heat into the surrounding tissue, US patent application publication 2010/0204698 A1 proposes active cooling of two movable electrodes, where thermoelectrical elements are used for the active cooling. The hot end of the thermoelectrical element is in turn cooled by fluid cooling to dissipate heat.

Tissue fusion instruments should, where possible, be easy to handle and have thin arms so that work can be carried out easily and reliably in confined spaces.

SUMMARY

An object of the embodiments disclosed herein is to create a tissue fusion instrument that is of simple design and which does not adversely affect surrounding tissue during tissue fusion.

The tissue fusion instrument in accordance with the embodiments disclosed herein has at least one electrode carrier that is connected to a power supply line or has a connecting mechanism for connecting a power supply line. Such connection mechanism may be sockets, terminals or the like.

The electrode carrier is designed, desirably, mechanically rigid and electrically conducting. It forms, for example, the mechanical supporting structure of an arm of a tissue fusion forceps. The rigidity of the electrode carrier is assured by the choice of a suitable material such as steel and by a suitable cross-section of the electrode carrier. A high flexural rigidity is desired to apply the necessary closing forces of a tissue fusion forceps. The electrode carrier has, for this purpose, a cross-section with a high area moment of inertia to yield a high bending resistance moment.

The electrode carrier is provided with an electrode that is brought into direct contact with the tissue to be fused. The electrode is connected to the electrode carrier electrically and mechanically. One or more punctiform connections are used for the connection. The punctiform connections are points at which the electrode carrier, or metal parts is/are in fixed connection to the electrode carrier, are firmly bonded to the electrode, for example, by soldering, adhesion or welding. The punctiform connection is thus, for example, adhesion/welding points, sequences of adhesion/welding points, or weld seams. No connection, however, is provided between the electrode carrier and the electrode over a large surface area.

The electrode carrier and the electrode together define a separation joint or a gap. In some embodiments, the electrode can be in surface contact with the electrode carrier, where the gap provided can prevent heat transfer from the electrode to the electrode carrier. With a connection that is solely punctiform, in the form of weld points or seams, little heat is transferred from the electrode to the electrode carrier.

The electrode can be a relatively thin, flat, profiled or curved plate that can be provided with one or more openings. The heat capacity of this electrode remains relatively low. During heating of tissue the electrode also heats up initially, but due to its low volume and associated low heat capacity it cools down again relatively quickly after use. The greater heat capacity of the electrode carrier is largely decoupled from the electrode by the solely punctiform substance connection between the electrode and the electrode carrier, so that the electrode carrier heats up to only a slight degree and can thus only return a small quantity of heat to the electrode. Thus, a good fusion result is obtained during tissue fusion, since a situation in which the electrode has too high a temperature at the time of gripping a vessel, which could bring about premature protein denaturation, is avoided.

Furthermore, the substantial prevention of heat flow from the electrode to the electrode carrier prevents the electrode carrier from heating up, for example, on its rear face, to the extent that it damages surrounding tissue. In addition, the electrode carrier can be provided with a plastic coating or be embedded in a plastic body. The thermal stress on the plastic is reduced by the measure in accordance with the embodiments disclosed herein. Moreover, the plastic ensures a further thermal and electrical insulation that further contributes to the fact that heat developing at the electrode is kept away from the rear face of the tissue fusion instrument/electrode carrier.

The gap between the electrode and the electrode carrier can vary in width depending upon the application. It can for example be zero (0), i.e., the electrode and the electrode carrier contact each other without any discernible distance between them. The electrode and the electrode carrier are then desirably in joint contact without a mechanical application of force i.e., mechanically stress-free. The distance between them can, however, also be between several tenths of a millimeter up to one millimeter, and if necessary greater. This distance is desirably metallically bridged only in a few places by the punctiform connections. A gaseous medium for example, air or a thermally insulating material such as a plastic, a ceramic or the like can be provided in the gap. The gap can be outwardly closed; for example, it can be bridged by plastic. The plastic with which the electrode carrier is coated or in which it is embedded can be used for this purpose.

The electrode carrier and the electrode can be designed from different materials, in particular from different metals. For example, the electrode material can be selected to have a low thermal capacity and a high heat conducting capability, so that the most uniform temperature distribution possible is achieved at the electrode. The electrode carrier can, for example, be selected on the basis of mechanical criteria to have a high rigidity, whereby other values for heat conductivity and thermal capacity can are obtained.

To form a distance between the electrode and the electrode carrier, the electrode, and additionally or alternatively the electrode carrier, may be provided with one or more projections, on which the corresponding firmly bonded connection points, i.e. for example weld points, are provided. It is, however, also possible, instead of these projections or in addition to them, to provide spacers, for example, in the form of one or more elements between the electrode and the electrode carrier on which the connection points are provided. The spacers can be made of metallic or non-metallic materials, or a combination of such materials, connectable by bonding, soldering, or welding. The connection points may be formed, for example, at front ends of narrow web-like or wire-like intermediate elements and thereby provide both a connection to the electrode and a connection to the electrode carrier.

A large number of embodiments are possible based on the options presented herein, in which the electrode and the electrode carrier manage without a flat material-based metallic connection, or contact one another without mechanical force. This creates a thermal barrier that hinders the flow of heat energy from the electrode to the rear face of the instrument. The punctiform connection between the electrode and the electrode carrier can also be an indirect connection, for example, by arranging a flat spacer between the electrode and the electrode carrier instead of a wire-like or web-like spacer. The metallic material connection from the electrode to the spacer can then be a punctiform connection and desirably provided at a different point from the spacer to the electrode carrier. It is thus possible to have two or more gaps between the electrode and the electrode carrier, where the above descriptions apply correspondingly to each gap.

The electrode can be provided with one or more openings that are used, for example, to accommodate further elements. These elements can be so-called inserts, for example, plastic or ceramic, which grip the vessel to be fused with a rib or other projections. One or more spacers can also be provided, for example, in the form of small ceramic pins, that prevent unwanted contact between the opposite electrodes of a tissue fusion forceps.

Spacers made of metal or other materials such as plastic or ceramic can be arranged between the electrode and the electrode carrier. These spacers can also be a part of elements that extend through the electrode and perform further functions, for example, gripping of the vessel and/or prevention of direct electrode contact between opposite electrodes of a tissue fusion forceps.

The surgical tissue fusion instrument in accordance with the embodiments disclosed herein can be a tissue fusion forceps or a laparoscopic instrument that has at least one movable tool arranged at the end of a long shaft. In principle, and in particular with laparoscopic instruments of this type, a cutting element can be additionally provided to separate the tissue being treated. The cutting function can be performed by one or more movable knives that are desirably arranged to be movable. A surgeon can thus intentionally cut through a coagulated vessel gripped between two electrodes with a movable knife.

BRIEF DESCRIPTION OF THE DRAWINGS

Numerous variations of the aforementioned methods are possible. Hereinafter, exemplary embodiments of the invention are explained in greater detail with reference to drawings, in which:

FIGS. 4 to 11 show, in vertical section, different embodiments of arms of fusion forceps or laparoscopic instruments;

FIG. 15 shows a further embodiment of an arm in a sectional perspective view;

FIG. 16 shows, in a sectional perspective view, an arm with ceramic spacers between the electrode and the electrode carrier;

FIG. 17 shows, in a vertical section, the arm according to FIG. 16; and

FIGS. 18 and 19 show, in a vertical section, further embodiments of an arm.

DETAILED DESCRIPTION

Figure 1:
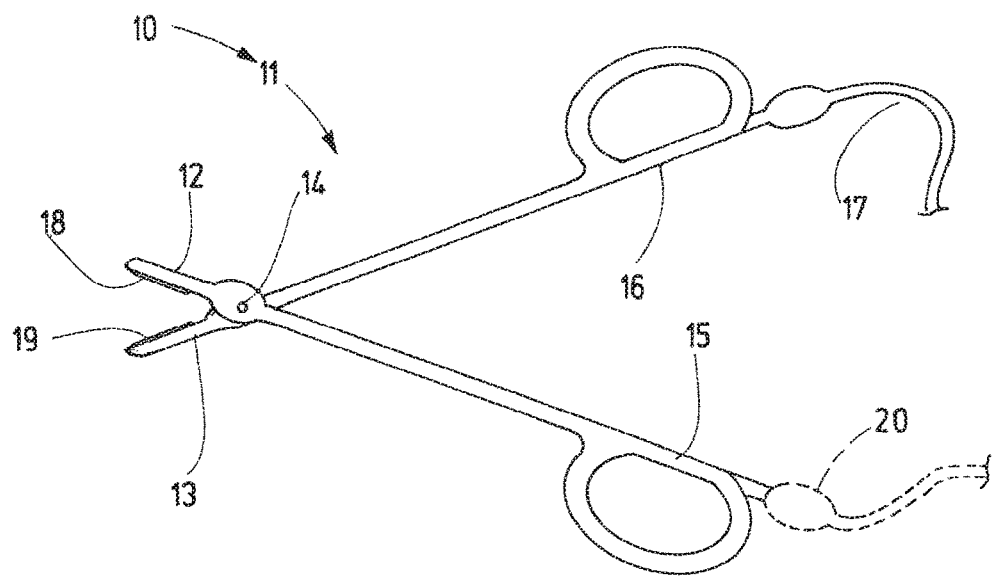
FIG. 1 shows a schematic representation of a tissue fusion forceps.

FIG. 1 shows an electrosurgical tissue fusion instrument 10 in the form of a tissue fusion forceps 11. The instrument 10 has a first arm 12 and a second arm 13, which are connected to each other by an articulated joint. In the illustrated embodiment, a hinged joint 14, for example, is used for the connection of the arms 12, 13. The arms 12, 13 are connected to handles 15, 16 by which the arms 12, 13 can be moved towards each other and away from each other. At least one of the handles 15, 16 is provided with an electrical supply line 17, through which electric current can be supplied to the electrodes 18, 19 on the arms 12, 13 for coagulation of a vessel gripped between said arms 12, 13. Alternatively to a design with a single (two-core) supply line 17 on the handle 16, each of the handles 15, 16 can be provided with a electrical supply line 17, 20 respectively (i.e., single-core).

Figure 2:
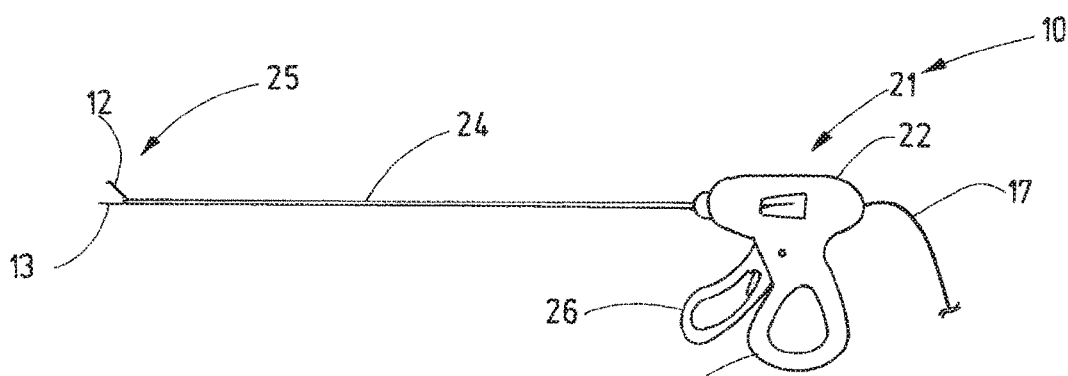
FIG. 2 shows a schematic representation of a laparoscopic fusion instrument.

As shown schematically in FIG. 2, the tissue fusion instrument 10 can also be designed as a laparoscopic instrument 21. The instrument 21 has a housing 22 provided with an electrical supply line 17 and with at least one handle 23 for handling by the physician. An elongated shaft 24 extends away from the housing 22 and has, at its end, a tool 25 for gripping, coagulating and if necessary cutting through a vessel. The tool 25 comprises two arms 12, 13 with the electrodes 18, 19 (not shown in detail in FIG. 2), which are arranged on the sides of the arms 12, 13 facing one another, as shown in FIG. 1. An operating mechanism, which can be actuated by a movable part 26 of the handle 23, extends through the shaft 24. Further operating elements can be provided on part 26 and/or the housing 22 as well as at the grip 23.

The following description of arm 12 applies correspondingly for arm 13 and for all embodiments of arm 12 that are described below. These embodiments may be used for both the tissue fusion forceps 11 and the laparoscopic instrument 21.

Arm 12 (FIG. 3) has an electrode carrier 27, that can be formed, for example, from a solid metal (e.g., steel, nickel-plated steel or the like). In the illustrated example, the electrode carrier 27 has an approximately rectangular or square cross-section and is tapered in the direction of its free end 28. The carrier can also have different cross sections. In particular, the carrier 27 can be rounded at its rear 29 facing away from the electrode 18. Irrespective of this, the carrier 27 has a surface 30 on the side facing the rear 29 to accommodate the electrode 18. The surface 30 can be a smooth, continuous or profiled surface, for example, napped, corrugated, grooved or otherwise profiled, which if necessary can have one or more recesses, for example in the form of blind holes. The electrode 18 is arranged on the surface 30. The electrode 18 is formed, in the simplest case, by a plate of metal; it can rest flat on the surface 30, so that a gap 32 is formed between the electrode 18 and the surface 30, but without any distance between them. However, a small or greater distance of, for example, a few hundredths or tenths of a millimeter can also be provided. The gap 32 can be empty or filled by, for example, a spacer of a non-metallic material.

The electrode 18 is connected to the arm 12 via punctiform connections 31, which are formed by, for example, adhesion points or weld points (e.g., laser weld points). At least two such connections 31 are desirably provided. If a plurality of such connections 31 are provided, then they extend in a row along the gap 32 formed between the electrode 18 and the electrode carrier 27. These connections 31 represent a firmly bonded metallic connection between the electrode 18 and the electrode carrier 27. This connection is used to mechanically fasten the electrode 18 to the electrode carrier 27 and for a reliable current flow between them. Because of the small cross section of the connections 31, however, only a low heat flow is possible through them.

The rear face of the electrode 18 facing the surface 30 is desirably glossy. Moreover, the surface 30 is desirably glossy. Heat transmission due to heat radiation via the gap 32 is in this manner minimized. Regardless of the width of the gap 32, a first barrier is thus formed for heat transmission. This barrier is also not bridged by direct thermal conduction if the rear face of the electrode 18 is free i.e., contacts the surface 30 without mechanical pre-stressing.

The front face 33 of the electrode 18 that is arranged facing away from the electrode carrier 27 can be smooth and continuous. It can, if necessary, also be serrated, napped, corrugated or otherwise profiled. In addition, it can be provided with one or more recesses into which elements, for example ceramic parts, can be inserted to perform certain functions (for example, gripping vessels or preventing contact between the two electrodes 18, 19 of the arms 12, 13). In addition, the electrode 18 can be formed differently from a flat plate and can have, for example, a slot-like recess inside that a knife, for example, is rotatably mounted to cut through coagulated vessels.

Figure 3:
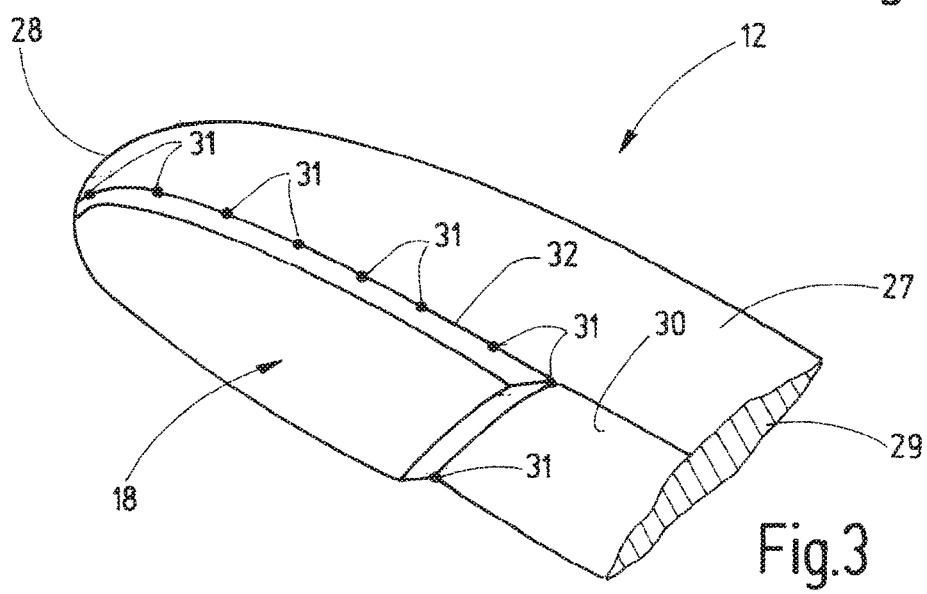
FIG. 3 shows a section of an arm of the fusion forceps according to FIG. 1, or of the instrument according to FIG. 2, in a schematic and simplified perspective view.

FIG. 4 shows a modified arm 12a, which is essentially based on arm 12 in FIG. 3. As can be seen, the electrode carrier 27 is again completely formed from an electrically-conductive material, for example, a metal or a metal alloy. The laser weld points used to form the connections 31 are arranged in a row extending around the gap 32 in a ring.

FIG. 5 shows a further modified arm 12b that has an electrode carrier 27 in the form of a metal section and a plastic body 34, into which the metal section of the electrode carrier 27 is embedded. The metal section is a U-shaped section. It has a web on which is provided the surface 30 used to accommodate the electrode 18. Two parallel limbs emanate from the web and extend into the plastic body 34. The electrode 18 is connected to the electrode carrier 27 by laser weld points. The laser weld points form the punctiform connections 31 that bridge the gap 32 and are used for mechanical and electrical connection. The plastic body 34 envelops the electrode carrier 27 and desirably extends over the gap 32 so that it covers and seals it all around.

Regardless of the cross-sectional shape of the arm 12, the gap 32 can be smaller or greater in size. This applies for all arm forms. FIG. 6 shows an example arm 12c with an electrode carrier 27 that is trapezoidal in cross section. The electrode 18 is arranged at a slight distance from the surface 30. The connections 31 bridge the gap 32 so formed. The resulting air gap acts in an insulating manner. In addition, as with all the embodiments described above or below, the facing surfaces of the electrode 18 and the electrode carrier 27 may be glossy, for example, polished, to minimize heat transmission through radiation.

One or more insulating bodies 35 can be arranged in the gap 32, as shown for arm 12d in FIG. 7. The insulating body 35 can be formed by, for example, a thin plate of ceramic, glass, plastic, foam or other poorly heat-conducting material. In addition, laser weld points or similar soldering or weld points act as connections 31 that bridge the gap 32.

The front surface 30 of the electrode carrier 27 intended to accommodate the electrode 18 does not necessarily have to have the same contours as the electrode 18. FIG. 8 illustrates an arm 12e where the electrode carrier 27 is formed as a T-section. The surface 30 to accommodate the electrode 18 is formed on the front face of the narrow web of the T-section in arm 12e. In addition, the connection between the electrode 18 and the electrode carrier 27 is formed by a series of connections 31, for example, in the form of laser weld points or short laser weld seams. A gap 32 without any distance or with a certain distance can be provided between the electrode carrier 27 and the electrode 18. A plastic body 34 that connects to the rear face of the electrode 18 and envelops the electrode carrier 27 is also provided.

The latter is also the case with arm 12f as shown in FIG. 9. The electrode carrier 27 has two V-shaped limbs 36, 37 that diverge from one another and are metallically bonded to the electrode 18 via the connections 31. The space 38 remaining between the limbs 36, 37 and the electrode 18 can be filled with air, plastic, can be evacuated, or a combination thereof. A gap from 0 mm to 1 mm can be present between the limbs 36, 37 and electrode 18, said gap being bridged by the connections 31. The limbs 36, 37 can be perforated to allow entry of gaseous or solid materials, desirably heat-insulating materials such as for example, plastic, into the space 38.

In arm 12g according to FIG. 10 or arm 12h according to FIG. 11, a gap from 0 mm to 1 mm or even greater can be present between the limbs 36, 37 and the electrode 18 and bridged by the connections 31. In contrast to arm 12f, the electrode carrier 27 according to FIG. 10 is semi-circular and according to FIG. 11 is designed V-shaped. Moreover, the area 38 can be filled with gas, be empty or be filled with plastic. The electrode carrier 27 can be provided with openings, not shown in detail, for introduction of a plastic filling.

Figure 12:
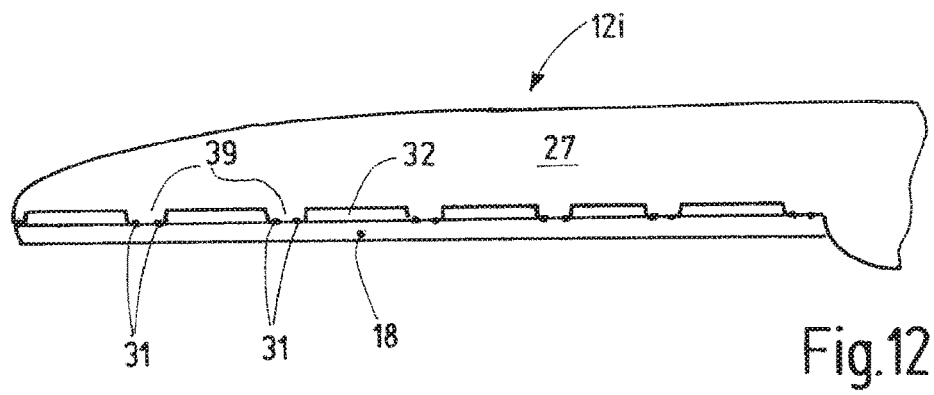
FIG. 12 shows a further embodiment of an arm in a simplified side view.

In all of the embodiments described above, in particular in the embodiments according to FIGS. 8 to 11, the edges of the electrode carrier 27 provided with the connections 31 can be straight or have a desired contour, for example a zigzag contour, a crenellation contour, a wave contour or the like. This enables an additional distance to be provided between, for example, the limbs 36, 37 and the electrode 18. The limbs 36, 37 approach each other only at the connection points 31 of the electrode 18 and otherwise maintain a greater distance therefrom. A configuration of this type is illustrated in FIG. 12 for arm 12i, which can for example be formed similarly to one of the arms according to FIGS. 3 to 7. Crenellation-like projections 39 extend at a distance to one another from the electrode carrier 27 to the electrode 18 to bridge the gap 32. The connections 31 are formed by, for example, laser weld points or laser weld seams that connect the projections 39 to the electrode 18. The crenellation-like projections 39 can extend along the outer edge of the electrode carrier 27. They can, however, also be arranged at another point. A crenellation structure of this type can, as mentioned above, also be provided at the limbs 36, 37 if the embodiments according to FIGS. 8 to 11 are used as a basis.

Figure 13:
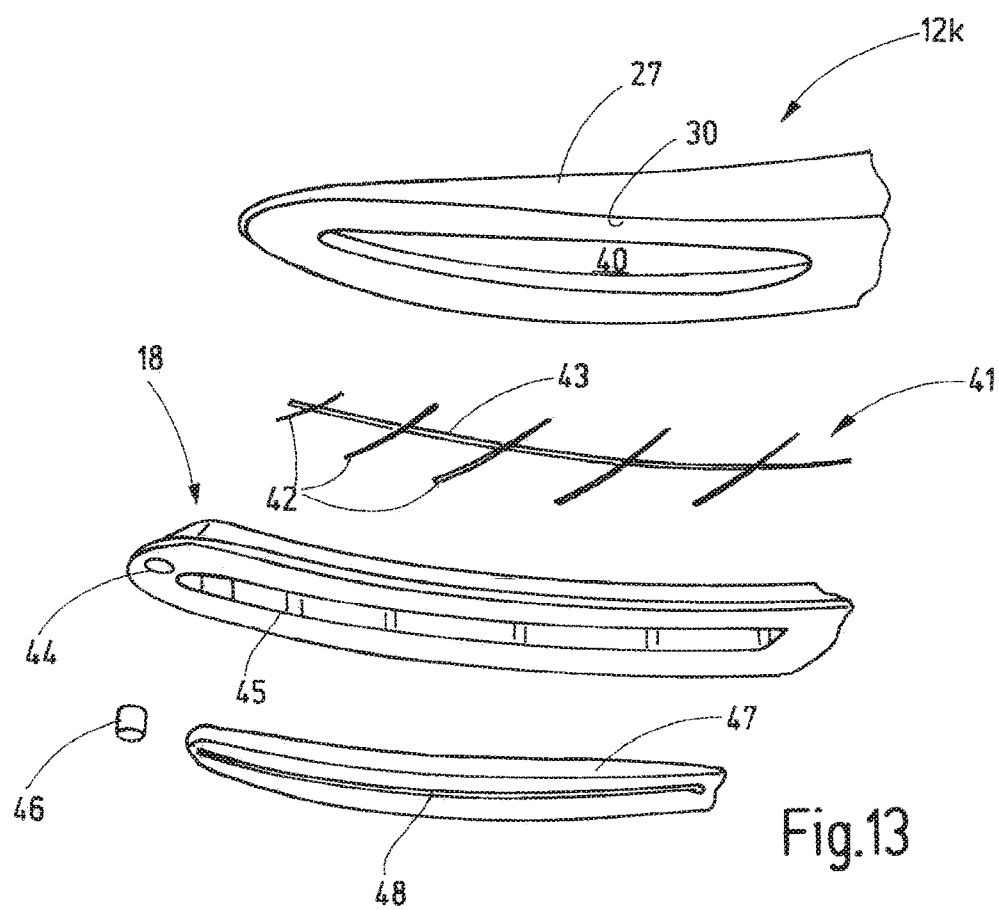
FIG. 13 shows a modified embodiment of an arm with a spacer in an exploded perspective view.
Figure 14:
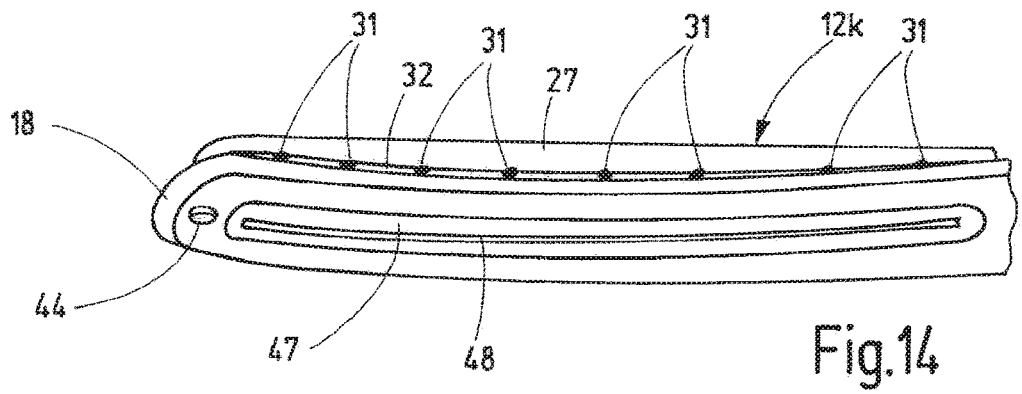
FIG. 14 shows the arm according to FIG. 13 in an assembled state.

FIGS. 13 and 14 illustrate a further embodiment of an arm 12k. This arm 12k has an electrode carrier 27 with a central elongated recess 40. The recess 40 interrupts the surface 30. A spacer 41 is arranged between the electrode 18 and the electrode carrier 27 and is formed by, for example, several wires 42 that can be interconnected by a connecting wire 43. The wires 42 form a ladder structure, a lattice structure or the like with the connecting wire 43. The electrode 18 has one or more openings 44, 45. The desirably cylindrical opening 44 is used, for example, to accommodate a ceramic pin 46 intended to prevent a short circuit between the electrodes facing one another. The opening 45 is used, for example, to accommodate an elongated insert 47 of plastic or ceramic used, for example, to clamp vessels between the electrodes 18, 19 and which has a central raised rib 48 for this purpose. In the assembled state, the front ends of the wires 42 of the spacer 41 are at the edge of the gap 32. The ends of the wires 42 can be converted into weld points using a laser beam or other suitable mechanism, creating a fixed punctiform metallic connection between the electrode 18 and the electrode carrier 27, as shown in FIG. 14. The wires 42 can thus act as spacers and, at the same time, as welding filler metal to produce the connections 31.

A further embodiment of the arm 12l is illustrated in FIG. 15. At least one further metallic element is arranged between the electrode 18 and the electrode carrier 27. For example, one, two or more thin plates 54, 55, rings, networks or the like can be arranged between the electrode 18 and the electrode carrier 27. Several gaps are therefore formed between the electrode 18 and the electrode carrier 27, each acting as heat barriers. The connection points 31 are, in each case, provided on the outside to bridge the gap and ultimately firmly bond the electrode 18 metallically to the electrode carrier 27.

Further variations are possible. For example, FIG. 16 shows an arm 12m in which the electrode carrier 27 is based on the model illustrated in FIG. 3. It is, however, also possible to use any other electrode carrier shown in FIGS. 4 to 7 as well as FIGS. 9 to 12.

With the example according to FIG. 16, spacers 49 are arranged between the electrode 18 and the electrode carrier 27, as can be seen in FIG. 17. These spacers 49 are formed, for example, by ceramic discs. From these, cylinder-like extensions 50 can extend through the openings provided in the electrode 18. The extensions 50 can be used, for example, to prevent vessels gripped between the electrodes 18, 19 from slipping as well as preventing contact between the electrodes 18, 19 opposite one another. The spacers 49 can be arranged in single rows or double rows or in another manner. The extensions 50 can be designed as a single piece with the ceramic discs and without a seam. Alternatively, the spacers 49 can be formed by rings of metal, plastic or ceramic mounted on pins 50 of metal, ceramic or plastic.

The gap remaining between the electrode 18 and the electrode carrier 27 is bridged by weld points that are arranged desirably on the outer edge of the gap 32. The surface 30 can, as shown, be formed flat or with a curvature at its edge in the direction of the electrode 18, to reduce the width of the gap 32 at the edge of the electrode 18. The edge of the surface 30 can also be provided with projections of all types (for example, crenellations according to FIG. 12).

Metallic spacer elements 51 can be provided instead of the ceramic spacers 49, as shown in FIG. 18 for arm 12n. The spacer elements 51 can be arranged in a single row or in a double row or in another manner. In addition, they can be formed from a disc 52 with an adjoining extension 53. The spacer elements 51 can, for example, be connected as one piece to the electrode carrier 27 or be butt-welded to it. They can also be formed by short screws that carry the disc 52 as a washer and are screwed into tapped holes of the electrode carrier 27 or are welded to its surface 30. The extensions 53 can extend through openings of the electrode 18 and be welded to the electrode 18 at their front face edge. The connection points 31 are therefore provided at the edge of openings of the electrode 18 rather than at the edge of the electrode 18. This principle is also transposable to almost all of the above-described embodiments, in particular to the embodiments according to FIGS. 4 to 12. The embodiment according to FIG. 18 can also be combined with the embodiment according to FIG. 16, in that in the latter pins or screws that correspond to the extensions 53 are provided in addition to the ceramic spacers 49 and extend through the electrode 18 to be welded to it.

FIG. 19 shows a further embodiment disclosed herein. The arm 12o in this embodiment has an electrode carrier 27 corresponding to the electrode carrier 27 according to FIG. 4. An electrode carrier according to FIGS. 5 to 7, FIG. 12 or FIG. 15, for example, can also be provided. The electrode 18, similar to the examples of FIGS. 13 and 14, has an elongated opening 45 inside which the insert 47 is arranged. The opening 45 is graduated. The insert 47 fills the further part (above the step) of the opening 45 and rests on the electrode carrier 27 or on its surface 30. The insert 47 is somewhat thicker than the distance between the step of the electrode 18 and of the surface 30, so that the insert 27 acts as a spacer. The connection points 31 represent a fixed connection between the electrode 18 and the electrode carrier 27.

During operation, a vessel is gripped between the arms 12, 13 and compressed. The tissue is heated by the supply of current (for example, high-frequency current) through the electrodes 18, 19, and the desired coagulation occurs. The heat generated at the tissue is transferred, at least in part, to the electrodes 18, 19, so that they also heat up. The heat, however, cannot flow so readily into the electrode carrier 27. The electrode carrier 27 therefore cools the electrode 18, 19 to a minor degree so that the desired thermal effect can develop unhindered in the vessel. The electrode carrier 27 absorbs very little heat, so that the arms 12, 13 heat up to hardly any appreciable degree on their outer faces. The thermal insulation due to the plastic body 34 or a plastic coating additionally prevents heat flowing from the arms 12, 13 into the biological tissue. Damage to tissue is thereby avoided.

The tissue fusion instrument 10 in accordance with embodiments disclosed herein has electrodes 18, 19 that are only connected to their electrode carrier 27 in a punctiform electrically-conducting manner and thus have a firmly bonded heat-conducting connection. The heat transmission from the electrodes 18, 19 to the respective electrode carrier 27 is thereby restricted. This firstly benefits the desired surgical outcome and secondly prevents parasitic heating of the surgical instrument and associated damage to the surrounding tissue.

What is claimed is:

1. A tissue fusion instrument comprising:
an electrode carrier, adapted to be connected to an electrical supply line; and
an electrode arranged directly on an electrically conductive external surface of the electrode carrier by a series of solely punctiform substance connections configured as weld points,
wherein the heat capacity of the electrode carrier is greater than the heat capacity of the electrode,
wherein the electrode and the electrode carrier are configured such that the transfer of heat from the electrode to the electrode carrier is limited by the solely punctiform substance connections between the electrode and the electrode carrier, and
wherein the series of weld points creates a gap between the electrode and the electrode carrier, the gap being bridged by projections.

2. The tissue fusion instrument according to claim 1, wherein the projections are provided at the electrode carrier.

3. The tissue fusion instrument according to claim 1, wherein the projections are provided at the electrode.

4. The tissue fusion instrument according to claim 1, wherein projections are provided in the electrode and the electrode carrier.

5. The tissue fusion instrument according to claim 1, wherein the weld points are provided at the end of the projections.

6. The tissue fusion instrument of claim 1, wherein the gap has a distance greater than zero.

7. A tissue fusion instrument comprising:
an electrode carrier;
an electrode having a first side, the first side of the electrode placed on a first side of the electrode carrier such that the first side of the electrode is opposite the first side of the electrode carrier;
at least one opening provided in the electrode; and
an electrical insulator arranged inside of the at least one opening,
wherein the electrical insulator projects from the opening as a spacer, and
wherein the spacer is arranged between the first side of the electrode carrier and the first side of the electrode.

8. The tissue fusion instrument of claim 7, wherein the electrical insulator comprises plastic.

9. The tissue fusion instrument of claim 7, wherein the electrical insulator comprises ceramic.

10. The tissue fusion instrument of claim 7, wherein the spacer is configured as a ceramic disc.

11. The tissue fusion instrument of claim 7, wherein the electrical insulator includes an extension that extends through the opening on a side of the electrode opposite the spacer.

12. The tissue fusion instrument of claim 11, wherein the electrical insulator, spacer and extension are configured as a single piece without a seam.

13. The tissue fusion instrument of claim 11, wherein the extension extends from the spacer and through the opening on the side of the electrode opposite the spacer.

14. The tissue fusion instrument of claim 7, wherein the arrangement of the spacer creates a gap between the electrode carrier and the electrode.

15. The tissue fusion instrument of claim 14, wherein the gap has a distance greater than zero.

* * * * *